United States Patent [19]

Pugh et al.

[11] 4,168,301

[45] Sep. 18, 1979

[54] DENTIFRICE BASED ON HIGH PARTICLE SIZE ALPHA-ALUMINA TRIHYDRATE

[75] Inventors: Brinley R. Pugh, Surbiton; Charles A. Watson, Ruislip, both of England

[73] Assignee: Lever Brothers Company, New York, N.Y.

[21] Appl. No.: 632,348

[22] Filed: Jul. 19, 1974

Related U.S. Application Data

[63] Continuation of Ser. No. 342,331, Mar. 19, 1973, abandoned, which is a continuation of Ser. No. 145,571, May 20, 1971, abandoned, which is a continuation-in-part of Ser. No. 62,197, Aug. 7, 1970, abandoned, which is a continuation of Ser. No. 707,325, Feb. 21, 1968, abandoned.

[30] Foreign Application Priority Data

Mar. 3, 1967 [GB] United Kingdom ............... 10248/67

[51] Int. Cl.² .................... A61K 7/16; A61K 7/18
[52] U.S. Cl. ....................... 424/49; 424/52; 424/57
[58] Field of Search ................... 424/49–58; 51/298–309

[56] References Cited

U.S. PATENT DOCUMENTS

| | | | |
|---|---|---|---|
| 2,010,910 | 8/1935 | Atkins | 424/49 |
| 2,550,207 | 4/1951 | Tainter | 424/49 |
| 2,818,371 | 12/1957 | Wessinger | 424/52 |
| 3,003,919 | 10/1961 | Broge | 424/49 |
| 3,034,967 | 5/1962 | Apperson et al. | 424/52 |
| 3,060,098 | 10/1962 | Gerson | 424/52 |
| 3,079,243 | 2/1963 | Ueltz | 51/298 |
| 3,121,623 | 2/1964 | Nesin | 51/298 |
| 3,151,027 | 9/1964 | Cooley et al. | 424/52 |
| 3,227,521 | 1/1966 | Carithers et al. | 424/49 |
| 3,325,368 | 6/1967 | Wood | 424/52 |
| 3,670,076 | 6/1972 | Muhler | 424/49 |
| 3,678,155 | 7/1972 | Clippingsdale et al. | 424/49 |
| 3,822,345 | 7/1974 | Murray et al. | 424/52 |
| 3,935,306 | 1/1976 | Roberts et al. | 424/49 |
| 3,955,942 | 5/1976 | Cordon et al. | 51/295 |
| 3,956,478 | 5/1976 | King et al. | 424/52 |
| 3,957,968 | 5/1976 | Cordon | 424/57 |

*Primary Examiner*—Shep K. Rose
*Attorney, Agent, or Firm*—Kenneth F. Dusyn; Berj A. Terzian; Melvin H. Kurtz

[57] ABSTRACT

The invention relates to a dentifrice which contains at least 40% by weight of abrasive agent of which at least 30% by weight of the dentifrice is alpha-alumina trihydrate having a particle size such that at least about 20%, and preferably at least about 25%, by weight of the particles have a size greater than 20 microns. The dentifrice when in the form of a toothpaste preferably contains as sole abrasive agent 45% to 60% by weight of particles of alpha-alumina trihydrate of gaussian distribution and weight median diameter of about 14 to about 25 microns.

11 Claims, No Drawings

DENTIFRICE BASED ON HIGH PARTICLE SIZE ALPHA-ALUMINA TRIHYDRATE

This a continuation of application Ser. No. 342,331, filed Mar. 19, 1973 now abandoned, and which is a continuation of Ser. No. 145,571, filed May 20, 1971, now abandoned, and which is a continuation-in-part of application Ser. No. 62,197 filed on Aug. 7, 1970 which is a continuation of application Ser. No. 707,325 filed on Feb. 21, 1968, all now abandoned.

This invention relates to dentifrices.

A principal component of a dentifrice is the cleaning agent commonly known as the abrasive or polishing agent. The function of an abrasive in a dentifrice is to remove adherent soils on the tooth surface. The effectiveness of a dentifrice in cleaning teeth is almost entirely dependent on the properties and proportions of the abrasive of the dentifrice. While the abrasiveness of the cleaning agent should be such that it is effective, its abrasiveness should not be so great that it will cause undue damage to underlying tooth enamel or to dentine, bearing in mind that dentifrices are intended to be used once or more times daily. Of particular importance is damage to tooth enamel since it represents all or virtually all of the exposed tooth surface. Nevertheless, the abrasiveness of the cleaning agent should not be such as to cause excessive damage to dentine in the case of those dentifrice users who have areas of tooth dentine exposed. Formulators are constantly searching for dentifrices which will have good cleaning properties and yet cause little damage to tooth structure.

There have been proposals in the past, particularly in the patent literature, to use hydrated alumina as a dentifrice abrasive and in fact there are dentifrices on the world market today which contain alpha-alumina trihydrate as the sole abrasive agent. It has now been discovered, however, that dentifrices based on alpha-alumina trihydrate of relatively large particle size have very good cleaning properties and, most unexpectedly, cause relatively low damage to tooth enamel.

The alpha-alumina trihydrate of this invention capable of giving high cleaning with relatively low enamel abrasion consists of particles having a size distribution such that at least about 20%, and preferably at least about 25%, by weight of the particles have a size greater than 20 microns. It is preferred that the particle size distribution of the alpha-alumina trihydrate is normal, that is gaussian, in which case the weight median diameter of the hydrated alumina particles should be from about 14 to about 25 microns, and in particular from about 16 to about 23 microns. (Weight median diameter is the size above which 50% by weight of the particles reside.) It is possible to use mixtures of different grades of alpha-alumina trihydrate resulting in an asymmetrical particle size distribution. However, the particle size distribution is desirably such that at least 50%, and preferably at least 70%, by weight of the particles have a size greater than 10 microns; 25% to 60%, preferably 30% to 50%, by weight have a size greater than 20 microns; 5% to 30%, preferably 10% to 30%, by weight have a size greater than 30 microns; and up to 15% by weight have a size greater than 40 microns. The upper limit of the size of the particles is determined mainly by consumer acceptability. If the content of vary large particles is excessive the dentifrice will produce an unacceptable gritty sensation in the mouth. For particles of gaussian distribution this may occur when about 70% by weight of the particles exceed 20 microns.

The dentifrices of this invention as stated above are based on the defined particle size alpha-alumina trihydrate, that is to say they contain this defined alumina as the sole or principal abrasive agent. However, minor proportions of abrasives other than alpha-alumina trihydrate can also be included in the dentifrices of the invention although, of course, having regard to their abrasiveness they must not be included in such an amount as to substantially impair the low enamel abrasion properties of the dentifrice imparted by the use of the special particle size alpha-alumina trihydrate of this invention. So that the dentifrice may exhibit good cleaning properties it is required that it should contain at least 40% by weight of abrasive of which at least 30% by weight of the dentifrice should be alpha-alumina trihydrate of which at least about 20% by weight has a particle size above 20 microns. Preferably, the amount of the alpha-alumina trihydrate is at least 40%, and in particular, for toothpastes, from 45% to 60% by weight of the dentifrice. Dentifrices in the form of powders usually comprise a much higher level of abrasive, and such desirably include the alpha-alumina trihydrate in amounts of from 80% to 99.5% by weight. In view of its very special high cleaning, low enamel abrasion properties it is preferred that the alpha-alumina trihydrate constitutes the sole abrasive cleaning agent. However, as stated other abrasives can be present in varying minor amounts (preferably not more than 10% by weight of the dentifrice) depending on their abrasiveness, although it is desirable that such supplementary abrasives should not have an abrasiveness to enamel greater than that of precipitated aragonitic chalk having a weight median diameter of 8 microns. Thus varying minor amounts of the conventional tooth abrasives aragonitic chalk, calcitic chalk, insoluble sodium metaphosphate and dicalcium phosphate dihydrate can also be included. It is known in formulating toothpastes to include small amounts of harder materials of very small size. These very small particles have no significant cleaning properties in their own right and are used to impart a lustre to the tooth surface. Such materials may also be included in the dentifrice of this invention.

Alpha-alumina trihydrate is made commercially by the Bayer process by precipitation from a solution of sodium aluminate. The precipitate is washed and dried at a low temperature and then ground to the desired particle size.

Other conventional ingredients can be included in dentifrices containing the special alpha-alumina trihydrate of this invention. Thus, in addition to the polishing agent, the dentifrice may contain optional ingredients such as soap or synthetic detergent, flavouring materials, buffers, sweetners, colouring materials and therapeutic materials, for example sodium fluoride, stannous fluoride and sodium monofluorophosphate. If the dentifrice is in the form of a paste it will contain a carrier, for example glycerine or sorbitol, and a binder, for example gum tragacanth, sodium carboxymethylcellulose, hydroxyethyl cellulose, Irish moss and its derivatives.

There will now be described experiments designed to compare the abrasiveness of various toothpastes to tooth dentine and tooth enamel, and experiments for assessing the ability of toothpastes to clean the tooth surface. A number of toothpastes designated herein A to P were used in the tests of which toothpaste D was one in accordance with this invention. The results of these experiments are set out in Table I.

Determination of Abrasiveness of a toothpaste towards dentine and enamel

The dentine or enamel specimens were exposed for 5 hours to a neutron flux of $10^{12}$ neutrons/cm$^2$, the temperature during irradiation not exceeding 40° C. After removal from the reactor, any $^{24}$Na activity was allowed to decay. A final specific activity of one to two millicurie per set of specimens was obtained under these conditions.

The radioactive specimens of dentine or enamel were mounted in four troughs of a brushing machine (employing a rectilinear brushing action in a horizontal plane) and surfaces of the specimens cleaned of debris etc. by brushing for 2,000 and 30,000 double brush strokes for dentine and enamel, respectively, in a slurry of a course chalk toothpaste (20 g toothpaste + 70 g of water). The brushing machine operated to give 150 double strokes per minute and the toothbrush loading was 280 g.

To eliminate any errors in the measurement of abrasion arising from a change from one toothpaste to another, prior to a test run with any particular toothpaste the specimen surface was given a prior brushing using a slurry of the toothpaste under test (20 g toothpaste + 70 g of water). The number of double brush-strokes was 1,000 and 20,000 for dentine and enamel, respectively. After pouring away this slurry, the troughs were washed thoroughly in distilled water. A slurry of the same toothpaste was then added to the troughs (20 g toothpaste + 10 g water). After ensuring the specimen was adequately covered, it was brushed for 500 (dentine) or 4,000 (enamel) double brush strokes. At the end of this run 15 ml of distilled water were added to the trough, mixed thoroughly with a glass rod, and a further 500 or 4,000 double brush strokes given. This procedure was repeated for a further three additions of 15 ml of distilled water. At the completion of the test the dentine and enamel had been brushed for 2,500 and 20,000 double brush strokes, respectively.

Four 1 g samples of the slurry from each trough were weighed and then dried by an infra-red heater. To avoid having to correct each count for activity decay which occurred from the beginning to the end of the whole series of experiments, all the samples from all the various toothpastes examined using a given set of irradiated specimens were retained. These were then counted within a short period of time using a suitable end-window geiger-counter.

The order for testing a series of toothpastes was to start and finish with a chalk reference toothpaste. This was done to ensure that the wear rate (with respect to the reference) had not altered from the beginning to the end of the whole run. If there were large differences between the two values for the reference, the results were discarded and a new set of irradiated specimens used to repeat the series.

A comparison was made between a standard paste and the test toothpastes. The standard comprised 40% by weight of a chalk abrasive. Analysis of variance on the results yielded the data from which a scale for ranking the toothpastes was obtained. On this scale the standard paste was arbitrarily assigned a value of 100.00. The ± values quoted with mean figures indicate 95% confidence limits. The values differ from toothpaste to toothpaste because of the conversion of the scale to assign the arbitrary value of 100.00 to the standard paste.

For toothpastes A, G, L, N and P dentine abrasion was not measured by the above method but by a weight-loss method. This involved weighing dentine samples before and after brushing. The weighing technique was carefully standardised to minimise the effect of variable water content of tooth dentine. These toothpastes were compared with the same chalk reference toothpaste as used in the above radiotracer method. In the weight-loss method 15,000 double brush strokes were found to give an adequate weight loss for the dentine specimens.

Assessment of the tooth cleaning ability of a toothpaste

The cleaning power of the abrasives were compared by an in vivo photographic test. A small panel of usually about 20 to 30 people was selected of people whose teeth stain. Their teeth were scaled and polished by a dental hygienist. The subjects then brushed their teeth with the test toothpaste and initial photographs of the 4 central upper and 6 central lower teeth then taken. The panel then used the test toothpaste in their normal manner for two weeks.

At the end of the test, the teeth were again brushed with the test toothpaste and rephotographed. A subject was then ready to test the next toothpaste in the comparison starting as before with a scaling and polishing of the teeth.

Considerable care was taken in the photography to obtain identical print quality. The photographs were black and white.

The assessments were carried out by two operators (trained in assessment of this type of photography) who worked together, alternately taking the roles of assessor and recorder. In this way, the assessor worked without knowledge of which photographs related to which toothpaste.

All the pairs of photographs relating to the comparison of two toothpastes were compared in succession, subject by subject, under standard conditions of simulated daylight in a colour matching cabinet.

The recorder set up two pairs of photographs (initial and final photographs for each toothpaste being compared) in the cabinet. The assessor then made comparisons between the levels of soil after use of the two toothpastes on each of the ten teeth. The assessor compared the differences between the areas of soil on the two final photographs, also taking into account the density of the soil and print intensities, and referring to the initial photographs to allow for any soil not completely removed at the beginning of the test.

The differences between each of the ten teeth assessed were scored and recorded on the scale 0 (no difference) to 3 (clearly discernible difference) with intervals of 0.5.

The scores for all ten teeth for each subject were added, and a positive or negative result was obtained for the two toothpastes being compared for cleaning efficiency. This means that if, in comparison, between, for example, a chalk and a dicalcium phosphate dihydrate-based toothpaste, it had been assumed that the chalk toothpaste was the more efficient, then a positive result indicated the presence of more soil after the use of the dicalcium phosphate dihydrate toothpaste. A negative result would be obtained where the assumption was found to be incorrect, i.e. more soil after the use of the chalk toothpaste.

This procedure was repeated until all possible intercomparisons between all the toothpastes tested had been carried out for every subject. Thus, if 5 toothpastes were being compared then there were 10 intercomparisons, and with 6 toothpastes there were 15 intercomparisons, for each subject, to be made by each assessor.

The results for every subject for all the paired comparisons were tabulated prior to statistical analysis. The analysis was made by a multiple regression technique leading to an analysis of variance, the calculations being made by computer. From the analysis the toothpastes were ranked in order of cleaning efficiency. The toothpaste with the least cleaning efficiency was assigned the arbitrary value of 0, and comparative values for the other toothpastes were calculated accordingly. By this means it was possible to rank the toothpastes used in the particular comparison in a hierarchy relative to each other.

An example of such an hierarchy is the following:

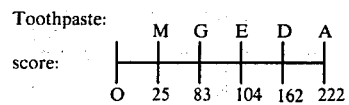

Toothpaste: M G E D A
score: 0 25 83 104 162 222

The score of zero is for an experimental low abrasive toothpaste. The difference required for 95 percent confidence is 30.

11 different hierarchies based on different selections of toothpastes were produced. Two toothpastes were common to each hierarchy: these were the low abrasive toothpaste and toothpaste D. As a result it was possible to reduce each hierarchy to a series of new hierarchies in which toothpaste D was arbitrarily given a cleaning score of 100.0 and the low abrasive toothpaste the value of 0. Where any given toothpaste occurred in more than one hierarchy the means of the scores in the new hierarchies was taken: this is the Mean Cleaning Score in Table I.

In Table I the results for toothpastes A to P are given together with an indication of the nature of the abrasive or abrasives of the toothpastes. All the toothpastes except A, D, E and O were, at least at the time of filing the original application Ser. No. 707,325, filed Feb. 21, 1978, now abandoned, sold on the world market. All the toothpastes contained from 45 to 55% by weight of abrasive except toothpastes E, F and I which contained, respectively, 40%, 42% and 30% by weight of abrasive. In the Table DCP stands for dicalcium phosphate and IMP stands for insoluble sodium metaphosphate.

The chalks used in the toothpastes in Table I were of varying particle size and chalk-type. For example, the chalk in toothpaste C was a mixture of 3.5 parts by weight of a precipitated calcium carbonate of aragonitic type and of weight median diameter of about 8 microns, and 1 part by weight of precipitated calcium carbonate of calcitic type and weight median diameter of about 13 microns. Toothpaste G contained the above aragonitic type and E and M the above calcitic type.

TABLE I

| Toothpaste | Abrasive | Dentine Abrasion Value | Mean Cleaning Score | Enamel Abrasion Value |
|---|---|---|---|---|
| A | Anhydrous DCP | 122 | 119 | 208** |
| B | Chalk | 117.8±13.3 | 113 | 150.6±29.4 |
| C | Mixture of Chalks | 105.4±12.6 | 94 | 73.2±20.3 |
| D | Alpha-alumina trihydrate | 96.3±12.0 (103.4±16.3*) | 100.0 | 45.0±17.0 (31.7±13.0*) |
| E | Chalk | 100.00 | 63 | 100.00 |
| F | Aluminium silicate | 80.4±14.4* | — | 55.6±15.2* |
| G | Chalk | 65 | 64 | — |
| H | Alpha-alumina trihydrate | 61.5±12.9* | — | 33.0±13.1* |
| I | Alpha-alumina trihydrate | 60.5±12.8* | — | 61.8±15.9* |
| J | Hydrated DCP/Chalk (10:1) | 58.1±9.7 | — | 31.0±15.4 |
| K | IMP/Silica/Aluminium silicate (26:14:3) | 57.4±10.2* | — | 86.8±18.4* |
| L | IMP/Hydrated DCP (1:1) | 44 | — | — |
| M | Hydrated DCP/Chalk (6:1) | 41.3±8.7 | 27 | 20.0±14.1 |
| N | Hydrated DCP/IMP (4:1) | 35 | 20 | — |
| O | Hydrated DCP | 33.3±8.2 | — | 18.7±13.9 |
| P | Alpha-alumina trihydrate | 24 | — | — |

*Results obtained with a different set of irradiated teeth specimens
**Result of a single experiment In Table I the toothpastes are ranked according to their abrasiveness to tooth dentine. It will be noted that this ranking correlates very closely with the ranking based on cleaning ability (the correlation coefficient "r" is significant to 1 in 1000).

Table I shows that while toothpaste D, which is a toothpaste according to this invention, has high cleaning ability, it has surprisingly low abrasiveness to tooth enamel compared with other high cleaning toothpastes.

Among the commercial toothpastes tested three contained alpha-alumina trihydrate, namely toothpastes H, I and P. The particle size analysis of the abrasives of samples of the toothpastes H, I and P are given in Table II below which also includes the analysis of a sample of the abrasives contained in the toothpastes B, C and D used in the tests.

TABLE II

| Size (Microns) | Toothpaste | Weight Percentage above Micron Size | | | | | |
| | | B | C | D | H | I | P |
|---|---|---|---|---|---|---|---|
| 45 | | 0 | 0.8 | 0.6 | 0 | 2.1 | 1.7 |
| 35 | | 1.5 | 1.6 | 11.5 | 10.3 | 7.8 | 2.6 |
| 28 | | 4.3 | 2.3 | 21.1 | 12.9 | 8.3 | 4.3 |
| 25 | | 6.5 | 2.9 | 27.0 | 14.1 | 8.8 | 5.1 |
| 23 | | 8.6 | 4.1 | 31.8 | 15.9 | 9.4 | 5.3 |
| 21 | | 13.3 | 6.7 | 39.8 | 16.6 | 9.8 | 6.1 |
| 19 | | 18.8 | 9.5 | 46.2 | 18.7 | 10.1 | 6.8 |

TABLE II-continued

| Size (Microns) | Toothpaste | Weight Percentage above Micron Size | | | | | |
|---|---|---|---|---|---|---|---|
| | | B | C | D | H | I | P |
| 17 | | 26.8 | 14.0 | 52.9 | 20.6 | 10.7 | 7.4 |
| 15 | | 36.6 | 21.2 | 62.2 | 22.2 | 11.5 | 8.1 |
| 13 | | 47.3 | 32.8 | 69.2 | 23.5 | 12.4 | 8.8 |
| 11 | | 56.3 | 48.9 | 76.6 | 25.9 | 13.6 | 10.0 |
| 9 | | 66.8 | 64.4 | 83.0 | 28.9 | 15.1 | 11.8 |
| 7 | | 78.3 | 79.1 | 88.2 | 35.9 | 16.5 | 13.7 |
| 5 | | 89.2 | 89.6 | 94.1 | 42.6 | 17.8 | 16.7 |
| 4.5 | | | | | 54.8 | | |
| 3.5 | | | | | 68.7 | | |
| 3 | | | | | | 37.1 | 45.5 |
| 2.5 | | | | | 97.1 | | |
| 1.5 | | | | | 98.6 | 68.6 | 72.7 |
| Weight median diameter (microns) | | 13.0 | 10.5 | 17.5 | 4.6 | 2.1 | 2.7 |

The particle size distribution of the abrasive of toothpaste D was gaussian whereas for the other three alumina toothpastes H, I and P the distribution was asymmetrical and appeared to consist of a mixture of a large average particle size material with a smaller average particle size material.

The above determination of cleaning ability and abrasiveness to dentine and enamel have been repeated using different batches of alpha-alumina trihydrate in accordance with this invention and these have given substantially the same high cleaning, low enamel abrasion results as indicated in Table I above. Typical analyses of batches of the alpha-alumina trihydrate in accordance with this invention are given in Table III below.

TABLE III

| Micron Size | Sample | Weight Percentage above Micron Size | | | | |
|---|---|---|---|---|---|---|
| | | 1 | 2 | 3 | 4 | 5 |
| 40.3 | | 5.2 | 3.3 | 5.0 | 7.1 | 13.5 |
| 32.0 | | 11.8 | 11.9 | 18.2 | 19.5 | 21.1 |
| 25.7 | | 25.8 | 27.1 | 36.1 | 34.3 | 33.6 |
| 20.2 | | 33.4 | 40.0 | 46.2 | 50.0 | 46.6 |
| 16.0 | | 51.6 | 59.7 | 61.5 | 69.6 | 58.3 |
| 12.7 | | 67.0 | 70.7 | 71.5 | 78.7 | 67.7 |
| 10.1 | | 81.0 | 81.8 | 81.4 | 86.1 | 75.8 |
| 8.0 | | 89.0 | 90.0 | 88.3 | 90.2 | 83.0 |
| 6.4 | | 94.0 | 94.1 | 93.4 | 95.0 | 90.1 |
| 5.0 | | 97.0 | 96.5 | 96.5 | 98.8 | 95.1 |
| 4.0 | | 98.0 | 98.2 | 98.3 | — | — |
| Weight median diameter (microns) | | 16.4 | 18.9 | 19.0 | 20.2 | 19.0 |

A further experiment was performed using toothpastes in accordance with the invention in which the level of the particles of alpha-alumina trihydrate greater than 20 microns was varied from about 50% by weight down to about 20% by weight.

The toothpastes used in this experiment (Toothpastes I to V) all contained as the sole abrasive component 50% by weight of alpha-alumina trihydrate and were of identical composition, differing only in the particle size of the alpha-alumina trihydrate used.

The dentine abrasion and enamel abrasion values for these toothpastes were determined by the method described above. The weight percentages of the alpha-alumina trihydrate particles above 20 microns in the toothpastes tested and the dentine abrasion and enamel abrasion data obtained are given below in Table IV.

TABLE IV

| Toothpaste | Weight % of alpha-alumina trihydrate particles above 20 microns | Dentine Abrasion Value | Enamel Abrasion Value |
|---|---|---|---|
| I | 50.3 | 100 | 21 |
| II | 30.0 | 100 | — |
| III | 33.3 | 109 | 34 |
| IV | 36.2 | 139 | 19 |
| V | 18.2 | 96 | 14 |

Particle size analysis data obtained from samples of the alpha-alumina trihydrates used in Toothpastes I to V are given below in Tables V and VI.

TABLE V

| Micron Size | Weight % of alpha-alumina trihydrate of Toothpaste II above micron size |
|---|---|
| 55–50 | 1.0 |
| 50–45 | 2.2 |
| 45–40 | 4.5 |
| 40–35 | 7.3 |
| 35–30 | 11.0 |
| 30–28 | 16.0 |
| 28–26 | 19.4 |
| 26–24 | 22.1 |
| 24–22 | 25.3 |
| 22–20 | 28.0 |
| 20–18 | 32.0 |
| 18–16 | 36.5 |
| 16–14 | 42.4 |
| 14–12 | 50.2 |
| 12–10 | 58.4 |
| 10–8 | 67.4 |
| 8–6 | 76.4 |
| 6–5 | 80.7 |
| 5–4 | 84.7 |
| 4–3 | 88.5 |
| 3–1.8 | 94.3 |
| Weight Median Diameter (microns) | 13.0 |

TABLE VI

| Micron Size | Weight % of alpha-alumina trihydrate of toothpaste above micron size | | | |
|---|---|---|---|---|
| Toothpaste: | I | III | IV | V |
| 70–60 | 1.9 | — | 0.3 | — |
| 60–50 | 5.9 | — | 1.5 | — |
| 50–46 | 7.6 | — | 2.7 | 0.1 |
| 46–42 | 10.2 | 0.25 | 3.5 | 0.4 |
| 42–38 | 15.6 | 1.0 | 4.8 | 0.6 |
| 38–34 | 21.3 | 2.0 | 7.7 | 0.8 |
| 34–30 | 27.1 | 4.5 | 11.7 | 1.4 |
| 30–26 | 34.3 | 9.9 | 17.7 | 3.1 |
| 26–22 | 41.2 | 19.2 | 25.8 | 7.5 |
| 22–18 | 50.3 | 33.3 | 36.2 | 18.2 |
| 18–14 | 61.7 | 48.7 | 49.2 | 36.3 |
| 14–10 | 74.5 | 65.9 | 64.5 | 58.1 |

TABLE VI-continued

| | Weight % of alpha-alumina trihydrate of toothpaste above micron size | | | |
|---|---|---|---|---|
| Micron Size  Toothpaste: | I | III | IV | V |
| 10–6 | 88.5 | 87.0 | 86.2 | 84.0 |
| 6–5 | 90.4 | 91.4 | 90.1 | 89.4 |
| 5–4 | 92.5 | 95.2 | 93.7 | 93.9 |
| 4–3 | 94.1 | 97.7 | 96.6 | 96.9 |
| 3–2 | 97.4 | 98.8 | 98.3 | 98.4 |
| Weight Median Diameter (microns) | 20.0 | 15.0 | 15.2 | 13.0 |

The results obtained showed that even when the percentage weight of the particles of alpha-alumina trihydrate above 20 microns was varied from about 50% down to about 20%, say 18%, the toothpaste still exhibited good cleaning properties (the dentine abrasion values obtained ranging from 96 to 139) and had low abrasiveness towards tooth enamel (the enamel abrasion values ranging from 14 to 34).

Experiments made on the effect of heating alpha-alumina trihydrate have shown that heating above 900° C. results in a loss of cleaning efficiency which is accompanied by a fall in the dentine abrasion value. Moreover, such heat treatment results in a substantial increase in enamel abrasion as is shown by the results given below in Table VII.

TABLE VII

| Sample | Mean Dentine Abrasion Value | Mean Enamel Abrasion Value |
|---|---|---|
| Untreated | 96 | 38 |
| 950° C. | 57 | 163 |
| 1000° C. | 48 | — |
| *1050° C. | 35 | 222 |

*This sample was used in the photographic cleaning assessment method described above and was found not to clean significantly differently from toothpaste M.

Examples of toothpaste compositions containing alpha-alumina trihydrate in accordance with this invention are the following:

EXAMPLE 1

| Ingredient | % by weight |
|---|---|
| Alpha-alumina trihydrate | 55.0 |
| Glycerine | 20.0 |
| Sodium carboxymethylcellulose | 1.0 |
| Sodium lauryl sulphate | 1.5 |
| Saccharin | 0.1 |
| Flavour | 0.9 |
| Water | to 100.0 |

EXAMPLE 2

| Ingredient | % by weight |
|---|---|
| Alpha-alumina trihydrate | 47.0 |
| Precipitated silica | 6.0 |
| Glycerine | 27.0 |
| Sodium carboxymethylcellulose | 0.8 |
| Saccharin | 0.2 |
| Sodium lauryl sulphate | 1.2 |
| Sodium monofluorophosphate | 0.8 |

-continued

| Ingredient | % by weight |
|---|---|
| Titanium dioxide | 0.5 |
| Flavour | 0.8 |
| Water | to 100.0 |

What is claimed is:

1. A dentifrice containing a total content of abrasive agent of at least 40% by weight, the abrasive agent comprising an amount of at least 30% by weight of the dentifrice of alpha-alumina trihydrate having a particle size distribution such that at least about 20% by weight of the particles have a size greater than 20 microns.

2. A dentifrice as claimed in claim 1, wherein at least about 25% by weight of the particles of the alpha-alumina trihydrate have a size greater than 20 microns.

3. A dentifrice as claimed in claim 1, wherein the particles of the alpha-alumina trihydrate have a normal gaussian distribution and have a weight median diameter of about 14 to about 25 microns.

4. A dentifrice as claimed in claim 3, wherein the particles of the alpha-alumina trihydrate have a weight median diameter of about 16 to about 23 microns.

5. A dentifrice as claimed in claim 2, wherein at least 50% by weight of the particles of the alpha-alumina trihydrate have a size greater than 10 microns; 25% to 60% by weight have a size greater than 20 microns; 5% to 30% by weight have a size greater than 30 microns; and up to 15% by weight have a size greater than 40 microns.

6. A dentifrice as claimed in claim 5, wherein at least 70% by weight of the particles of the alpha-alumina trihydrate have a size greater than 10 microns; 30% to 50% by weight have a size greater than 20 microns; and 10% to 30% by weight have a size greater than 30 microns.

7. A dentifrice as claimed in claim 1, containing at least 40% by weight of abrasive agents consisting substantially entirely of alpha-alumina trihydrate having a particle size distribution such that at least about 20% by weight of the particles have a size greater than 20 microns.

8. A dentifrice as claimed in claim 7, wherein the alpha-alumina trihydrate is present in an amount of 45% to 60% by weight of the dentifrice, the dentifrice being in the form of a toothpaste.

9. A dentifrice as claimed in claim 1, wherein the alpha-alumina trihydrate is the sole abrasive agent of the dentifrice.

10. A dentifrice as claimed in claim 1 in the form of a toothpaste and containing as sole abrasive agent 45% to 60% by weight of an alpha-alumina trihydrate having a gaussian particle size distribution and having a weight median diameter of about 16 to about 23 microns.

11. A dentifrice as claimed in claim 1 containing a total content of abrasive of at least 40% by weight, the abrasive agent comprising (a) an amount of at least 30% by weight of the dentifrice is alpha-alumina trihydrate having a particle size distribution such that at least about 20% by weight of the particles have a size greater than 20 microns, and (b) not more than 10% by weight of a supplementary abrasive being selected from the group of abrasives precipitated silica, aragonitic chalk, calcitic chalk, insoluble sodium metaphosphate and dicalcium phosphate dihydrate.

* * * * *